United States Patent [19]
Nickel et al.

[11] 3,931,409
[45] Jan. 6, 1976

[54] COMPOSITION AND METHOD FOR TREATMENT OF HYPERURICEMIA

[75] Inventors: Ardie R. Nickel, Fishkill; Franklin J. Rosenberg, Bethlehem; James H. Ackerman, Rensselaer, all of N.Y.

[73] Assignee: Sterling Drug Inc., New York, N.Y.

[22] Filed: Nov. 4, 1974

[21] Appl. No.: 520,630

Related U.S. Application Data

[62] Division of Ser. No. 348,531, April 6, 1973, Pat. No. 3,892,800.

[52] U.S. Cl. .............. 424/309; 424/316; 424/319; A61K/31/195
[51] Int. Cl.² ............. A61K 31/24; A61K 31/205
[58] Field of Search ................. 424/309, 316, 319

[56] References Cited
UNITED STATES PATENTS

| | | | |
|---|---|---|---|
| 3,100,226 | 8/1963 | Raman et al. | 260/518 A |
| 3,703,546 | 11/1972 | Leaper et al. | 260/518 A |

*Primary Examiner*—Donald B. Moyer
*Attorney, Agent, or Firm*—Thomas L. Johnson; B. Woodrow Wyatt

[57] ABSTRACT

Trichloroamino(and acylamino)phenylalkanoic acids or esters, useful as uricosuric agents, are prepared by chlorination of the corresponding aminophenylalkanoic acids or esters, followed, if desired, by N-acylation and N-alkylation.

10 Claims, No Drawings

COMPOSITION AND METHOD FOR TREATMENT OF HYPERURICEMIA

This application is a division of copending application Ser. No. 348,531, filed Apr. 6, 1973 now U.S. Pat. No. 3,892,800.

This invention relates to novel trichloroamino(and acylamino)phenylalkanoic acids and esters and salts thereof, to methods for their preparation, and to compositions and methods for treatment and prophylaxis of hyperuricemic conditions in mammals by administration of said novel compounds.

The compounds of the invention have the following structural formula

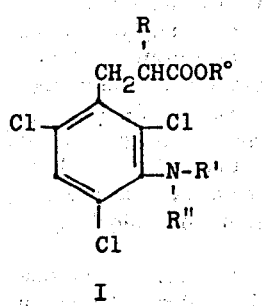

I wherein:
R, R° and R'' are hydrogen or alkyl of 1–4 carbon atoms; and
R' is hydrogen or alkanoyl of 1–6 carbon atoms, R' being limited to alkanoyl when R'' is alkyl.

Also within the purview of the invention are pharmaceutically acceptable salts of the compounds of formula I where R° is hydrogen, for example, the sodium, magnesium, calcium or N-methylglucamine salts.

When R, R° and/or R'' stand for alkyl of 1–4 carbon atoms, the alkyl can be straight or branched and thus includes methyl, ethyl, propyl, isopropyl, butyl, isobutyl, secondary-butyl and tertiary-butyl. The alkyl groups are preferably primary or secondary.

When R' stands for alkanoyl of 1–6 carbon atoms, the alkanoyl can be straight or branched and thus includes formyl, acetyl, propionyl, butyryl, isobutyryl, valeryl, caproyl, 4-methylpentanoyl, and the like.

The compounds of the invention can be prepared from a known class of starting materials having the formula

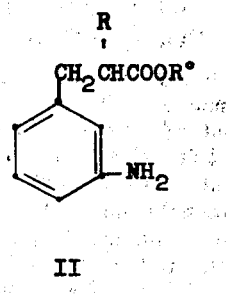

II wherein R and R° have the meanings given hereinabove. The first step is a chlorination carried out by treating a compound of formula II with a source of elementary chlorine. The source of elementary chlorine can be chlorine itself, hypochlorous acid, N-halo compounds, sulfuryl chloride or the like. Gaseous chlorine ($Cl_2$) is preferred for economic reasons. The chlorination takes place at ambient temperatures in an inert solvent, preferably a non-aqueous solvent to prevent an excessive amount of oxidative side-reactions. Preferred solvents are the lower-alkanoic acids, especially acetic acid. In the latter solvent, the intermediates of formula II readily react with chlorine to produce the 2,4,6-trichloro derivatives (I; R' and R'' are hydrogen). The chlorination of compounds of formula II where R° is hydrogen produces a minor proportion of a byproduct derived from further chlorination of the trichloroaniline derivative and having the formula:

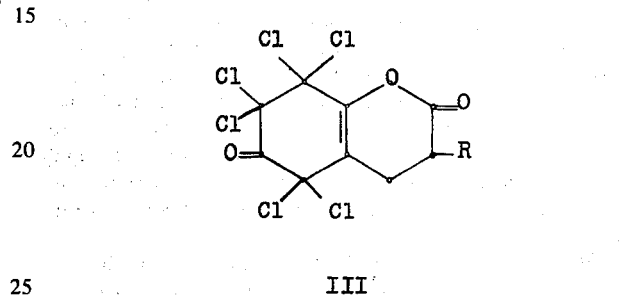

III

The compounds of formula III are readily separated from the respective compounds of formula I (R°, R' and R'' are hydrogen), produced in the chlorination reaction, by virtue of the fact that the former are more highly soluble in non-polar organic solvents. The compounds of formula III possess antibacterial and antifungal activity.

The compounds of formula I where R' is lower-alkanoyl of 1–6 carbon atoms and R'' is hydrogen are prepared by interacting a compound of formula I where both R' and R'' are hydrogen with the appropriate acid anhydride or acid halide (chloride or bromide). A preferred procedure comprises heating the compound of formula I where R' and R'' are hydrogen with an acid anhydride in the presence of a catalytic amount of a strong acid such as sulfuric or perchloric acid at a temperature between about 50° and 100°C. If N-formyl compounds (R' is COH) are desired, a mixture of formic acid and acetic anhydride ("formic acetic anhydride") is employed.

The compounds of formula I where R' is alkanoyl of 1–6 carbon atoms and R'' is alkyl of 1–4 carbon atoms are prepared by interacting a compound of formula I where R' is alkanoyl of 1–6 carbon atoms and R'' is hydrogen with a dialkyl sulfate ($R''_2SO_4$), alkyl halide (R''Br or R''I), alkyl alkanesulfonate (R''methanesulfonate or the like) or alkyl arylsulfonate (R''benzenesulfonate, R''naphthalenesulfonate or the like) under aqueous alkaline conditions. The alkylation takes place readily under ambient temperature conditions.

The compounds of formula I where R° is alkyl of 1–4 carbon atoms can be prepared by conventional esterification procedures from the corresponding compounds where R° is hydrogen, for example, by interacting the acid with the appropriate alcohol in the presence of a strong acid or with a diazoalkane. The esterification can be carried out at the intermediate stage to form compounds of formula II where R° is alkyl. The esters in turn can serve as intermediates for the corresponding acids by hydrolytic procedures.

The salts of the compounds of formula I where R° is hydrogen can be prepared by neutralization with the appropriate base, e.g. sodium hydroxide, magnesium hydroxide, calcium oxide or hydroxide, or N-methylglucamine.

The structures of the compounds of the invention (formulas I and III) were established by the modes of synthesis, elementary analysis and the interpretation of their infrared and nuclear magnetic resonance spectra.

The compounds of formula I are uricosuric agents and are therefore useful in the treatment and prophylaxis of hyperuricemia in mammals by causing increased elimination of uric acid and a reduction in the blood levels of uric acid.

Abnormally high blood levels of uric acid (hyperuricemia) frequently lead to pathological conditions caused by deposition of urate salt crystals in the kidneys (lithiasis, kidney stones) and in the joints (gout). To alleviate and prevent these painful afflictions it is necessary to increase the rate of elimination of uric acid from the animal organism and thereby decrease the concentration of uric acid in the blood to normal levels. This can be accomplished by the administration of uricosuric agents such as probenecid and allopurinol.

It has been reported that polyiodinated acids and salts thereof useful as X-ray contrast agents for visualizing the gallbladder, such as iopanoic acid, sodium ipodate and iodipamide, have uricosuric properties. However, the use of these substances in the treatment and prophylaxis of hyperuricemia is contraindicated because repeated administration of these highly iodinated compounds may cause gradual accumulations of iodine residues in the animal organism thereby upsetting the balance of endocrine functions such as the thyroid, and interfering with certain tests of thyroid function. The chlorinated compounds of the instant invention do not possess this drawback.

The compounds of formula I have been shown to be uricosuric agents when tested by their effect in excretion of uric acid upon oral (0.2 millimoles per kilogram) and/or intravenous (0.1 millimoles per kilogram) administration to Cebus monkeys. The compounds are effective at doses far below those which elicit any toxic manifestations in the animals. The most active compounds, a preferred group of formula I where R° and R'' are hydrogen, R is alkyl and R' is alkanoyl, have activities comparable to that of the standard uricosuric agent, probenecid, upon oral administration, and have advantages over probenecid such as longer duration of action and lower incidence of gastric irritation as measured by their gastric irritation-ulcerogenesis potential in rats.

A further aspect of this invention thus relates to compositions comprising the compounds of formula I for the treatment and prophylaxis of hyperuricemia in mammalian organisms, and to a method for treatment of said mammalian organisms with said compositions.

When intended for oral use, the compounds of the invention are mixed with conventional solid excipients such as lactose, magnesium stearate, silicate powder, cellulose, and any of a variety of various known buffering agents, bonding agents, flavoring agents, dispersants, preservatives, antioxidants and coating materials conventionally used in the art of pharmacy. The mixture is compressed into tablets or placed in capsules to produce unit dosage forms.

When intended for intravenous use, a water-soluble salt form of the compounds of the invention is dissolved in sterile aqueous medium suitable for intravenous injection and the solution stored in a sealed vial or ampoule until used.

The best modes of carrying out the invention are set forth in the following examples which should be considered as illustrative of but not limiting the invention.

EXAMPLE 1

3-Amino-2,4,6-trichloro-α-ethylhydrocinnamic acid [I; R is $C_2H_5$, R°, R' and R'' are H].

Chlorine gas was passed into a solution of 250 g. of 3-amino-α-ethylhydrocinnamic acid in 2,500 ml. of glacial acetic acid held at a temperature of 17°–20°C. until the weight of chlorine taken up was about 300 g. (about 5 hours' time). The reaction mixture was concentrated in vacuo to a volume of about 700 ml. and cooled to 16°C. The solid which had separated (31 g. partially chlorinated starting material) was removed by filtration, and the filtrate was added to 2.5 liters of water. The latter mixture was extracted with ethyl acetate, and the extract was washed twice with water, dried over anhydrous magnesium sulfate and concentrated in vacuo to remove the solvent. The residue was recrystallized from cyclohexane to give 101 g. of 3-amino-2,4,6-trichloro-α-ethylhydrocinnamic acid, m.p. 118°–121°C.

The filtrate from the cyclohexane recrystallization was diluted with 100 ml. of n-hexane, cooled to 4°C. and the dissolved material induced to crystallize, affording 48 g. of solid, m.p. 154°–159°C. The latter solid was slurried in 500 ml. of boiling cyclohexane and filtered. The filtrate was decolorized with activated charcoal and cooled to 5°C. There separated 12 g. of 3-ethyl-5,5,7,7,8,8-hexahydro-3,4,7,8-tetrahydro-2H-1-benzopyran-2,6(5H)-dione (III; R is $C_2H_5$), m.p. 163°–167°C.

According to the foregoing procedure methyl 3-amino-α-ethylhydrocinnamate, isopropyl 3-amino-α-ethylhydrocinnamate, or butyl 3-amino-α-ethylhydrocinnamate (prepared by esterification of 3-amino-α-ethylhydrocinnamic acid with the appropriate alkanol) can be chlorinated to give, respectively, methyl 3-amino-2,4,6-trichloro-α-ethylhydrocinnamate [I; R is $C_2H_5$, R° is $CH_3$, R' and R'' are H], isopropyl 3-amino-2,4,6-trichloro-α-ethylhydrocinnamate [I; R is $C_2H_5$, R° is $CH(CH_3)_2$, R' and R'' are H], or butyl 3-amino-2,4,6-trichloro-α-ethylhydrocinnamate [I; R is $C_2H_5$, R° is $(CH_2)_3CH_3$, R' and R'' are H].

EXAMPLE 2

3-(n-Butyramido)-2,4,6-trichloro-α-ethylhydrocinnamic acid [I; R is $C_2H_5$, R° and R'' are H, R' is $COCH_2CH_2CH_3$].

A mixture of 670 g. of 3-amino-2,4,6-trichloro-α-ethylhydrocinnamic acid, 296.6 g. of n-butyric anhydride and 610 ml. of isopropyl acetate was warmed with stirring to 40°C. Concentrated sulfuric acid (5 ml.) was then added, and an exothermic reaction occurred which caused the temperature of the mixture to rise to 65°C. after 15 minutes. Heat was then applied to the reaction mixture to hold it at 65°C. for 10 minutes longer, and then 137 ml. of methanol was added to decompose the excess butyric anhydride. The reaction mixture was diluted with 1 liter of isopropyl acetate, cooled to 25°C. and diluted further with 2.2 liters of cyclohexane. The latter solution was cooled to 10°C. and the product allowed to crystallize therefrom. The solid product was collected by filtration and washed with a 1:1 mixture of isopropyl acetate and n-hexane; then slurried in 2.5 liters of cold water while 150 ml. of 28% ammonium hydroxide solution was added gradually until the solid had dissolved. The solution thus formed was acidified slowly with hydrochloric acid, and the precipitated acid product was extracted with ethyl acetate (3.5 liters), and the extract washed with 5% hydrochloric acid and with water, dried over anhydrous magnesium sulfate and concentrated to remove the solvent. There was thus obtained 643 g. of 3-(n-butyramido)-2,4,6-trichloro-α-ethylhydrocinnamic acid, m.p. 127°–130°C. The product was recrystallized from acetonitrile to afford 554 g., m.p. 128°–131°C.

According to the foregoing procedure, methyl 3-amino-2,4,6-trichloro-α-ethylhydrocinnamate, isopropyl 3-amino-2,4,6-trichloro-α-ethylhydrocinnamate, or butyl 3-amino-2,4,6-trichloro-α-ethylhydrocinnamate can be acylated with butyric anhydride to give, respectively, methyl 3-(n-butyramido)-2,4,6-trichloro-α-ethylhydrocinnamate [I; R is $C_2H_5$, R° is $CH_3$, R' is $COCH_2CH_2CH_3$, R'' is H], isopropyl 3-(n-butyramido)-2,4,6-trichloro-α-ethylhydrocinnamate [I; R is $C_2H_5$, R° is $CH(CH_3)_2$, R' is $COCH_2CH_2CH_3$, R'' is H], or butyl 3-(n-butyramido)-2,4,6-trichloro-α-ethylhydrocinnamate [I; R is $C_2H_5$, R° is $(CH_2)_2CH_3$, R' is $COCH_2CH_2CH_3$, R'' is H].

A solution of 245 g. of 3-(n-butyramido)-2,4,6-trichloro-α-ethylhydrocinnamic acid in 5 liters of methyl isobutyl ketone was warmed to 98°–102°C., and a solution of 36 g. of sodium methoxide in 500 ml. of methanol was added gradually over a period of 30 minutes. The methanol was distilled off, and heating and removal of solvents was continued for 30 minutes until the pot temperature had reached 115°C. Methyl isobutyl ketone (2 liters) was added, the mixture cooled to 60°C. and seeded, and then allowed to cool slowly while the product crystallized. After crystallization was complete, the supernatant was decanted, and the solid residue slurried with methyl isobutyl ketone and with isopropyl acetate, collected and dried at 80°C. in vacuo to give 185 g. of sodium 3-(n-butyramido)-2,4,6-trichloro-α-ethylhydrocinnamate, m.p. 176°–214°C. (decompn.).

3-(n-Butyramido)-2,4,6-trichloro-α-ethylhydrocinnamic acid reacts with molar equivalent amounts of magnesium hydroxide, calcium hydroxide or N-methylglucamine to give, respectively, the magnesium, calcium or N-methylglucamine salts of said acid.

EXAMPLE 3

3-Acetamido-2,4,6-trichloro-α-ethylhydrocinnamic acid [I; R is $C_2H_5$, R° and R'' are H, R' is $COCH_3$].

A mixture of 390 g. of 3-amino-2,4,6-trichloro-α-ethylhydrocinnamic acid (Example 1), 161 g. of acetic anhydride, 4 liters of glacial acetic acid and 4 ml. of concentrated sulfuric acid was stirred at room temperature for 18 hours. The reaction mixture was warmed 30 minutes at 40°C. and then 8 liters of water was added. The reaction mixture was cooled to 10°C., and the solid product was collected by filtration, washed three times with 200 ml. of water, then twice with 200 ml. of n-pentane, and dried in vacuo at 60°C. for 4.5 hours. The 459 g. of solid thus obtained was recrystallized from 1,400 ml. of acetonitrile, using activated charcoal for decolorizing purposes, and dried at 50°C. under high vacuum for 16 hours and at 75°C. under high vacuum for 9 hours, to give 397 g. of 3-acetamido-2,4,6-trichloro-α-ethylhydrocinnamic acid, m.p. 142°–148°C. A further recrystallization from isopropyl acetate afforded a sample with m.p. 142°–147°C.

3-Acetamido-2,4,6-trichloro-α-ethylhydrocinnamic acid had uricosuric activity comparable to probenecid in Cebus albifrons monkeys. The compound was active intravenously as the sodium salt and orally as the sodium salt or as the acid. Upon oral administration of 0.2 millimoles per kilogram of the acid form to pentobarbital-anesthetized monkeys peak uricosuric activity was seen 40 to 60 minutes later. Comparable doses of probenecid showed maximum uricosuric activity between 120 and 140 minutes after medication.

Crystals of 3-acetamido-2,4,6-trichloro-α-ethylhydrocinnamic acid were stable to dry heat, non-hygroscopic, light stable and compatible with 12 common tablet and capsule excipients. After 7 days at 70°C. no apparent physical changes or chemical decomposition was detected for 1:1 mixtures of 3-acetamido-2,4,6-trichloro-α-ethylhydrocinnamic acid with the following excipients: talc, Avicel (cellulose, microcrystalline form), sodium bicarbonate, starch, lactose, mannitol, dextrose, sucrose, citric acid, magnesium stearate, sodium lauryl sulfate and dicalcium phosphate.

No decomposition was detected after 5 days at 70°C. for 10 mg/ml buffered aqueous suspensions (pH 2.9 and 5.0) and for 10 mg/ml buffered aqueous solutions (pH 6.7 and 8.3) of 3-acetamido-2,4,6-trichloro-α-ethylhydrocinnamic acid.

By procedures similar to those of Examples 2 and 3, 3-amino-2,4,6-trichloro-α-ethylhydrocinnamic acid can be caused to react with isobutyric anhydride or caproic anhydride to give, respectively, 3-isobutyramido-2,4,6-trichloro-α-ethylhydrocinnamic acid [I; R is $C_2H_5$, R° and R'' are H, R' is $COCH(CH_3)_2$], or 3-caproylamino-2,4,6-trichloro-α-ethylhydrocinnamic acid [I; R is $C_2H_5$, R° and R'' are H, R' is $CO(CH_2)_4CH_3$]. Alternatively, the latter compound can be prepared by reacting 3-amino-2,4,6-trichloro-α-ethylhydrocinnamic acid with caproyl chloride in toluene solution.

EXAMPLE 4

3-Amino-2,4,6-trichlorohydrocinnamic acid [I; R, R°, R' and R'' are H] was prepared from 20 g. of 3-aminohydrocinnamic acid and about 22.55 g. of chlorine in 400 ml. of acetic acid according to the procedure described above in Example 1. There was obtained 7 g. of 3-amino-2,4,6-trichlorohydrocinnamic acid, m.p. 154°–155°C., after several recrystallizations from isopropyl alcohol.

The byproduct, 5,5,7,7,8,8-hexachloro-3,4,7,8-tetrahydro-2H-1-benzopyran-2,6(5H)-dione (III; R is H), produced by further reaction of chlorine with the 3-amino-2,4,6-trichlorohydrocinnamic acid, was present in the residues and mother liquors from the separation of the latter in the foregoing preparation; however, said byproduct could be prepared directly from the 3-amino-2,4,6-trichlorohydrocinnamic acid by treating an acetic acid solution of the latter with chlorine gas. In this way 22.50 g. of 3-amino-2,4,6-trichlorohydrocinnamic acid was converted to 16.91 g. of 5,5,7,7,8,8-hexachloro-3,4,7,8-tetrahydro-2H-1-benzopyran-2,6(5H)-dione, colorless needles, m.p. 166°–169°C. after several recrystallizations from isopropyl alcohol. This compound was found to have antibacterial activity in vitro against Staphylococcus aureus and antifungal activity in vitro against Trichophyton mentagrophytes,

*Aspergillus niger* and *Candida albicans*.

According to the procedures of Examples 1 and 4, 3-amino-α-isopropylhydrocinnamic acid or 3-amino-α-butylhydrocinnamic acid can be chlorinated to give 3-amino-2,4,6-trichloro-α-isopropylhydrocinnamic acid [I; R is $CH(CH_3)_2$, $R°$, $R'$ and $R''$ are H], or 3-amino-2,4,6-trichloro-α-butylhydrocinnamic acid [I; R is $(CH_2)_3CH_3$, $R°$, $R'$ and $R''$ are H]; and the respective by-products 3-isopropyl-5,5,7,7,8,8-hexahydro-3,4,7,8-tetrahydro-2H-1-benzopyran-2,6(5H)-dione [III; R is $CH(CH_3)_2$], or 3-butyl-5,5,7,7,8,8-hexahydro-3,4,7,8-tetrahydro-2H-1-benzopyran-2,6(5H)-dione [III; R is $(CH_2)_3CH_3$].

The intermediate 3-amino-α-isopropylhydrocinnamic acid and 3-amino-α-butylhydrocinnamic acid can be prepared from m-nitrobenzaldehyde via a Perkin reaction with the appropriate acid anhydride, followed by catalytic reduction of the resulting m-nitrocinnamic acid derivative, as described in U.S. Pat. No. 2,705,726.

EXAMPLE 5

3-(n-Butyramido)-2,4,6-trichlorohydrocinnamic acid [I; R, $R°$ and $R''$ are H, $R'$ is $COCH_2CH_2CH_3$].

A mixture of 10.89 g. of 3-amino-2,4,6-trichlorohydrocinnamic acid (Example 4), 11 ml. of butyric anhydride and 55 ml. of butyric acid was heated on a water bath at 68°C. until solution was complete. Concentrated sulfuric acid (0.5 ml.) was then added, and the mixture was heated and stirred for 2 hours. The reaction mixture was cooled to room temperature and the solid product which separated was collected by filtration and washed with acetic acid. The solid product was recrystallized from acetonitrile to give 9.21 g. of 3-(n-butyramido)-2,4,6-trichlorohydrocinnamic acid, colorless flakes, m.p. 172°–174°C. A further recrystallization gave a sample with the m.p. 176°–178°C.

By analogous procedures, 3-amino-2,4,6-trichloro-α-isopropylcinnamic acid or 3-amino-2,4,6-trichloro-α-butylcinnamic acid can be acylated with butyric anhydride to give, respectively, 3-(n-butyramido)-2,4,6-trichloro-α-isopropylcinnamic acid [I; R is $CH(CH_3)_2$, $R°$ and $R''$ are H, $R'$ is $COCH_2CH_2CH_3$], or 3-(n-butyramido)-2,4,6-trichloro-α-butylcinnamic acid [I; R is $(CH_2)_3CH_3$, $R°$ and $R''$ are H, $R'$ is $COCH_2CH_2CH_3$].

EXAMPLE 6

3-(N-Methylacetamido)-2,4,6-trichloro-α-ethylhydrocinnamic acid [I; R is $C_2H_5$, $R°$ is H, $R'$ is $COCH_3$, $R''$ is $CH_3$].

A mixture of 15 g. of 3-acetamido-2,4,6-trichloro-α-ethylhydrocinnamic acid (Example 3) and 84 ml. of 10% aqueous sodium hydroxide was stirred until solution was complete. A solution of 9 ml. of dimethyl sulfate in 12 ml. of acetone was then added, and the mixture was stirred for 30 minutes. Additional 15 ml. of 10% sodium hydroxide, 3 ml. of dimethyl sulfate and 3 ml. of acetone were added, and the mixture was stirred for 30 minutes longer. The reaction mixture was cooled in an ice bath and treated with 3N hydrochloric acid until the mixture was strongly acid. The separated solid was collected by filtration and dried in a 60° oven. The dried solid (16 g.) was dissolved in hot isopropyl acetate, filtered while hot to remove some insoluble material, and cooled to afford 7.10 g. of 3-(N-methylacetamido)-2,4,6-trichloro-α-ethylhydrocinnamic acid, m.p. 121°–125°C. A further recrystallization from isopropyl acetate gave a sample with the m.p. 131°–134°C.

EXAMPLE 7

3-(N-Ethylacetamido)-2,4,6-trichloro-α-ethylhydrocinnamic acid [I; R and $R''$ are $C_2H_5$, $R°$ is H, $R'$ is $COCH_3$] was prepared from 15 g. of 3-acetamido-2,4,6-trichloro-α-ethylhydrocinnamic acid (Example 3), 12 ml. of diethyl sulfate, 90 ml. of 10% sodium hydroxide and 15 ml. of acetone, stirred 2 hours at room temperature. There was thus obtained 5.71 g. of 3-(N-ethylacetamido)-2,4,6-trichloro-α-ethylhydrocinnamic acid, m.p. 96°–111°C., when recrystallized from cyclohexane.

By procedures similar to those of Examples 6 and 7, 3-acetamido-2,4,6-trichloro-α-ethylhydrocinnamic acid can be caused to react with diisopropyl sulfate or butyl iodide to give, respectively, 3-(N-isopropylacetamido)-2,4,6-trichloro-α-ethylhydrocinnamic acid [I; R is $C_2H_5$, $R°$ is H, $R'$ is $COCH_3$, $R''$ is $CH(CH_3)_2$], or 3-(N-butylacetamido)-2,4,6-trichloro-α-ethylhydrocinnamic acid [I; R is $C_2H_5$, $R°$ is H, $R'$ is $COCH_3$, $R''$ is $(CH_2)_3CH_3$]; and methyl 3-(n-butyramido)-2,4,6-trichloro-α-ethylhydrocinnamate can be caused to react with dimethyl sulfate to give methyl 3-(N-methyl-n-butyramido)-2,4,6-trichloro-α-ethylhydrocinnamate [I; R is $C_2H_5$, $R°$ and $R''$ are $CH_3$, $R'$ is $COCH_2CH_2CH_3$]. To the extent that any hydrolysis of the ester group is caused by the aqueous alkali present, the free acid fraction can be re-esterified by conventional means, as with diazomethane.

We claim:

1. A composition for the treatment and prophylaxis of hyperuricemia in a mammal which comprises in unit dosage form a uricosurically effective amount of a compound in an inert diluent, said compound having the formula

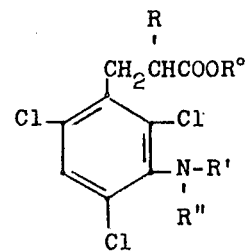

wherein:
R, $R°$ and $R''$ are hydrogen or alkyl of 1–4 carbon atoms; and
$R'$ is hydrogen or alkanoyl of 1–6 carbon atoms, $R'$ being limited to alkanoyl when $R''$ is alkyl;
or pharmaceutically acceptable salts thereof where $R°$ is hydrogen.

2. A composition according to claim 1 wherein the inert diluent is a solid excipient.

3. A composition according to claim 1 wherein the compound is a salt and the inert diluent is a sterile aqueous medium suitable for intravenous administration.

4. A composition according to claim 1 which comprises a uricosurically effective amount of 3-(n-butyramido)-2,4,6-trichloro-α-ethylhydrocinnamic acid in a solid excipient.

5. A composition according to claim 1 which comprises a uricosurically effective amount of 3- acetamido-2,4,6-trichloro-α-ethylhydrocinnamic acid in a solid excipient.

6. A method for treatment and prophylaxis of hyperuricemia in a mammal, which comprises administering to said mammal a uricosurically effective amount of a compound in an inert diluent, said compound having the formula

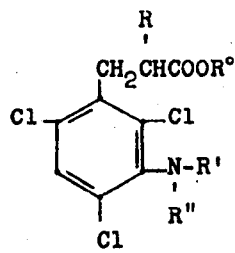

wherein:

R, R° and R'' are hydrogen or alkyl of 1–4 carbon atoms; and

R' is hydrogen or alkanoyl of 1–6 carbon atoms, R' being limited to alkanoyl when R'' is alkyl;

or pharmaceutically acceptable salts thereof where R° is hydrogen.

7. A method according to claim 6 in which the inert diluent is a solid excipient and the administration is by the oral route.

8. A method according to claim 6 in which the compound is a salt, the inert diluent is a sterile aqueous medium, and the administration is by the intravenous route.

9. A method according to claim 6 which comprises administering orally a uricosurically effective amount of 3-(n-butyramido)-2,4,6-trichloro-α-ethylhydrocinnamic acid in a solid excipient.

10. A method according to claim 6 which comprises administering orally a uricosurically effective amount of 3-acetamido-2,4,6-trichloro-α-ethylhydrocinnamic acid in a solid excipient.

* * * * *